(12) United States Patent
Mansfield et al.

(10) Patent No.: US 8,187,243 B2
(45) Date of Patent: May 29, 2012

(54) DISPOSABLE ABSORBENT ARTICLE CONTAINING AN UNAPERTURED SKINLESS ELASTOMERIC LAYER

(75) Inventors: Todd Leon Mansfield, Cincinnati, OH (US); Ebrahim Rezai, Mason, OH (US); James Thomas Bader, Hamilton, OH (US); Adam Daniel Schmidtz, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 755 days.

(21) Appl. No.: 11/478,235

(22) Filed: Jun. 29, 2006

(65) Prior Publication Data

US 2007/0005037 A1   Jan. 4, 2007

Related U.S. Application Data

(60) Provisional application No. 60/694,835, filed on Jun. 29, 2005.

(51) Int. Cl.
*A61F 13/15* (2006.01)
*A61F 13/20* (2006.01)

(52) U.S. Cl. .......... 604/385.27; 604/385.01; 604/385.24

(58) Field of Classification Search .......... 604/358, 604/385.01, 385.22–385.24, 385.27
See application file for complete search history.

(56) References Cited

U.S. PATENT DOCUMENTS

| | | | |
|---|---|---|---|
| 3,396,699 A | 8/1968 | Beebe et al. |
| 3,848,594 A | 11/1974 | Buell |
| 3,860,003 A | 1/1975 | Buell |
| 3,911,173 A | 10/1975 | Sprague, Jr. |
| 3,929,135 A | 12/1975 | Thompson |
| 4,084,018 A | 4/1978 | Karr |
| 4,324,246 A | 4/1982 | Mullane et al. |
| 4,342,314 A | 8/1982 | Radel et al. |
| 4,388,075 A | 6/1983 | Mesek et al. |
| 4,463,045 A | 7/1984 | Ahr et al. |
| 4,515,595 A | 5/1985 | Kievit et al. |
| 4,573,986 A | 3/1986 | Minetola et al. |
| 4,606,928 A | 8/1986 | Dunford et al. |

(Continued)

FOREIGN PATENT DOCUMENTS

WO   WO 94/14395 A1   7/1994

(Continued)

OTHER PUBLICATIONS

International Search Report.

*Primary Examiner* — Michele M Kidwell
(74) *Attorney, Agent, or Firm* — Andrew A Paul; John P. Colbert; Dara M. Kendall (57) ABSTRACT

The present invention relates to a disposable absorbent article comprising a chassis having a front waist region, a back waist region, and a crotch region between the front and back waist regions, said chassis having two opposing longitudinal edges and two perpendicularly placed end edges, said chassis further comprising:
  a. a liquid permeable topsheet spanning at least the crotch region;
  b. a backsheet spanning at least the crotch region;
  c. an absorbent core disposed between said topsheet and backsheet; and
  d. a elastic member disposed along at least one opposing longitudinal edge in either the front waist or back waist region of said chassis wherein said member comprises an unapertured, skinless elastomeric layer wherein said layer exhibits an Energy Recovery Value of at least about 0.77.

15 Claims, 4 Drawing Sheets

U.S. PATENT DOCUMENTS

| | | | |
|---|---|---|---|
| 4,609,518 A | 9/1986 | Curro et al. | |
| 4,610,678 A | 9/1986 | Weisman et al. | |
| 4,629,643 A | 12/1986 | Curro et al. | |
| 4,662,874 A * | 5/1987 | Korpman | 604/370 |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,834,735 A | 5/1989 | Alemany et al. | |
| 4,834,741 A | 5/1989 | Sabee | |
| 4,842,666 A | 6/1989 | Werenicz | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,026,364 A | 6/1991 | Robertson | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,755 A | 12/1993 | Bodicky | |
| 5,269,775 A | 12/1993 | Freeland et al. | |
| 5,306,266 A | 4/1994 | Freeland | |
| 5,342,338 A | 8/1994 | Roe | |
| 5,382,461 A | 1/1995 | Wu | |
| 5,383,872 A | 1/1995 | Roessler et al. | |
| 5,387,207 A | 2/1995 | Dyer et al. | |
| 5,397,318 A | 3/1995 | Dreier | |
| 5,422,172 A | 6/1995 | Wu | |
| 5,499,978 A | 3/1996 | Buell et al. | |
| 5,507,736 A | 4/1996 | Clear et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| H1670 H | 7/1997 | Aziz et al. | |
| 5,643,588 A | 7/1997 | Roe et al. | |
| 5,653,703 A | 8/1997 | Roe et al. | |
| 5,843,068 A | 12/1998 | Allen et al. | |
| 5,865,823 A | 2/1999 | Curro | |
| 5,897,545 A | 4/1999 | Kline et al. | |
| 5,938,648 A | 8/1999 | LaVon et al. | |
| 5,941,864 A | 8/1999 | Roe | |
| 5,957,908 A | 9/1999 | Kline et al. | |
| 5,968,025 A | 10/1999 | Roe et al. | |
| 5,977,430 A | 11/1999 | Roe et al. | |
| 5,997,520 A | 12/1999 | Ahr et al. | |
| 6,004,306 A | 12/1999 | Robles et al. | |
| 6,013,063 A | 1/2000 | Roe et al. | |
| 6,037,281 A * | 3/2000 | Mathis et al. | 442/394 |
| 6,068,702 A | 5/2000 | Bertellotti et al. | |
| 6,096,668 A * | 8/2000 | Abuto et al. | 442/328 |
| 6,120,487 A | 9/2000 | Ashton | |
| 6,120,489 A | 9/2000 | Johnson et al. | |
| 6,168,584 B1 | 1/2001 | Allen et al. | |
| 6,217,692 B1 | 4/2001 | Kling | |
| 6,316,687 B1 | 11/2001 | Davis et al. | |
| 6,410,129 B2 * | 6/2002 | Zhang et al. | 428/318.6 |
| 6,432,098 B1 | 8/2002 | Kline et al. | |
| 6,680,422 B2 | 1/2004 | Roe | |
| 6,716,441 B1 | 4/2004 | Osborne et al. | |
| 2003/0105446 A1 * | 6/2003 | Hutson et al. | 604/385.22 |
| 2003/0233082 A1 | 12/2003 | Kline et al. | |
| 2004/0092902 A1 * | 5/2004 | Hoffman et al. | 604/385.101 |
| 2004/0102755 A1 | 5/2004 | Morman et al. | |
| 2005/0177123 A1 | 8/2005 | Catalan | |

FOREIGN PATENT DOCUMENTS

| | | |
|---|---|---|
| WO | WO 95/16746 A1 | 6/1995 |
| WO | WO 95/24173 A2 | 9/1995 |

* cited by examiner

DISPOSABLE ABSORBENT ARTICLE CONTAINING AN UNAPERTURED SKINLESS ELASTOMERIC LAYER

CROSS REFERENCE TO RELATED APPLICATIONS

This application claims the benefit of U.S. Provisional Application No. 60/694,835, filed Jun. 29, 2005.

FIELD OF THE INVENTION

The present invention relates to disposable absorbent articles that include a chassis and an elastic member disposed along at least one opposing longitudinal edge in either the front waist or back waist region of said chassis wherein said member comprises an unapertured, skinless elastomeric layer wherein said layer exhibits an Energy Recovery Value of at least about 0.77.

BACKGROUND OF THE INVENTION

Disposable absorbent articles are well known for their utility in aiding in the containment of body exudates including urine, menses, and feces. As such these articles take various forms including diapers, pull-on training pants, incontinence garments, and sanitary napkins. One important feature for each of these articles is conforming fit. It is imperative that these articles conform to the portion of the body that acts as the anchor to hold the article in place during wear. It is widely known that provision of an elastic portion of such an article serves well to engage the article to a wearer's body.

Conventional disposable absorbent articles have included strand elastics and elastomeric films to serve this engaging function in various areas of the articles. These areas include at the leg opening, the waist opening, the outer cover, and side panels (which are typically elasticized). In particular, when an elastomeric film is typically employed as an elastic member, it includes an elastomeric core layer flanked by substantially inelastic skin layers on opposing sides or surfaces. These inelastic skin layers, when stretched, allow for reduced friction and blocking of the overall film. This reduced blocking aids in increasing the processsability of the film as well as providing an increased softness to the touch of the film which is desirable when the wearer's skin comes in contact with the area of the article that includes the film. This approach, however, requires additional polymers to form the skin layers and these bring in additional costs for manufacturing.

Another approach which allows for the manufacture of an elastic laminate includes the use of a release liner with a single layer elastomeric film. In the instance described above as well as in the case of a release liner, possible raw materials for this elastomeric film are elastomers, SBS block copolymers, SIS block copolymers, polyurethane, ethylene copolymers and similar materials. As one would expect, in the absence of one or more inelastic skin layers, the elastomeric films are relatively sticky and hard to handle during processing. In order to facilitate conversion as a roll of stock material, a release liner has to be added which covers at least on one side the elastomeric layer. The release liner can be made from a number of materials, including but not limited to silicone paper. When further converting the film material, in most instances the release liner is separated from the elastomeric film, removed, and wound up for disposal or re-use. Only then may the elastomeric film be laminated to a nonwoven web that is friendlier to the skin of the ultimate wearer of a product containing the film. In such instances, however, the handling of an elastomeric monofilm or single layer film paired with a release liner subsequently requires another mechanism to facilitate handling of the layer for future lamination with one or more nonwovens.

SUMMARY OF THE INVENTION

Applicant has therefore found that certain disposable absorbent articles are useful for meeting this unmet need of producing disposable absorbent articles that include elastic members comprising elastomeric films manufactured with mechanisms for aiding in the non-blocking that is required to facilitate the lamination process of such films with nonwoven layers. Such articles comprise a chassis having a front waist region, a back waist region, and a crotch region between the front and back waist regions, said chassis having two opposing longitudinal edges and two perpendicularly placed end edges, said chassis further comprising:

a. a liquid permeable topsheet spanning at least the crotch region;

b. a backsheet spanning at least the crotch region;

c. an absorbent core disposed between said topsheet and backsheet; and d. a elastic member disposed along at least one opposing longitudinal edge in either the front waist or back waist region of said chassis wherein said member comprises an unapertured, skinless elastomeric layer wherein said layer exhibits an Energy Recovery Value of at least about 0.77.

DETAILED DESCRIPTION OF THE INVENTION

For the present invention, detailed herein are various definitions which are intended to aid in the interpretation of the claimed subject matter.

As used herein, the term "absorbent article" refers to devices which absorb and contain body exudates, and more specifically, refers to devices which are placed against or in proximity to the body of the wearer to absorb and contain the various exudates discharged from the body. Such devices include, but are not limited to, diapers, training pants, adult incontinence products, sanitary napkins, and pantiliners.

As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

As used herein, the term "disposable" refers to absorbent articles which generally are not intended to be laundered or otherwise restored or reused as an absorbent article (i.e., they are intended to be discarded after a single use and, preferably, to be recycled, composted or otherwise disposed of in an environmentally compatible manner).

A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 220, shown in FIG. 4.

Elastic Member

The disposable absorbent article of the present invention comprises chassis having a front waist region, a back waist region, and a crotch region between the front and back waist regions, the chassis has two opposing longitudinal edges and two perpendicularly placed end edges, and the chassis further comprises: a. a liquid permeable topsheet spanning at least the crotch region; b. a backsheet spanning at least the crotch region; c. an absorbent core disposed between said topsheet and backsheet; and d. a elastic member disposed along at least one opposing longitudinal edge in either the front waist or back waist region of said chassis wherein said member comprises an unapertured, skinless elastomeric layer wherein said layer exhibits an Energy Recovery Value of at least about 0.77.

The elastic member comprises a skinless elastomeric layer that is unapertured. As used herein "skinless" means that the subject layer is a monofilm, monolayer or single ply layer that has not been coextruded with or bonded to any additional polymeric film layers on one or both of its surfaces. As used herein "unapertured" refers to the absence of apertures or holes in one more surfaces of the elastomeric layer. As used herein "adhesively bonded" or "adhesively laminated" refers to the laminate wherein an adhesive is used to bond the elastic member to the nonwoven or nonwovens. This elastic member may be situated between the substantially inelastic members where at least one substantially inelastic member is disposed between the elastic member and the chassis. These one or more substantially inelastic members may serve as anchoring portions of the elastic member to the chassis. In essence, the substantially inelastic members are used to fix fastening or closing elements (e.g., hooks, tapes, etc.) to one portion of the chassis while attaching a complementary gripping element for the fastening element to a corresponding portion of the chassis. The elastic member of the present invention may be produced via depositing a full-sized sheet of the unapertured, skinless elastomeric layer onto one or more sheets of a nonwoven carrier web and employing adhesive lamination between such layers. This composite laminate is then incrementally stretched or ring-rolled (as disclosed in U.S. Pat. Nos. 5,422,172 and 5,382,461) and cut into smaller sections which are then utilized as elastic members per the present invention. Another manner of producing the elastic members, which results in an even larger economical savings since less film is utilized, involves employing one or more strips of the unapertured, skinless elastomeric layer in lieu of an entire sheet. In this instance, the strip(s) are positioned suitably and laminated adhesively to the nonwoven web. Again, this composite laminate can be stretched in the same manner as described above.

Before the elastomeric layer, however, is laminated to the one or more nonwoven carrier web layers, the elastomeric layer is stored in packaging (i.e., wound onto a roll or festooned into a container) for subsequent use in the above-described lamination process. In order to facilitate this process, Applicant has found that treating the elastomeric layer with one or more anti-blocking treatments facilitates the handling of the elastomeric layer and the lamination process in general. The anti-blocking treatments include application of powders to the surfaces of the elastomeric film, roughening the film's surface topography by embossing, roughening the film's surface topography by addition of filler particles to the bulk of the film, addition of chemical species that decrease tack ("slip agents" or "release agents"), application of non-tacky materials to one or both surfaces of the film, for example, non-pressure-sensitive adhesives, waxes, rigid polymers (e.g., glassy, highly crystalline or densely crosslinked polymers such as polystyrene, isotactic polypropylene or phenol-formaldehyde polymers, respectively.) These anti-blocking treatments facilitate the laminating process by preventing the elastomer layer from sticking to itself during roll unwinding or de-festooning until such time as it is adhesively laminated to one or more nonwoven webs.

Suitable powders for addition to one or more surfaces of the elastomeric layer are selected from the group consisting of talc, mica, mullite, calcium carbonate, silica, powdered polyethylene, corn starch, barium sulfate, gypsum, activated carbon, polyolefin, alginate, aluminum silicate, bentonite, carbon black, carbon nanotubes, chalk, cobalt acetate, dicalite perlite, dolomite calfix, flour, graphite, hydroxy ethyl cellulose, kaolin, polyethylene wax, polyvinyl alcohol, rice flour, starch, modified starch, super absorbent, vermiculite, wax powder, oxides of bismuth, cerium, zirconium, manganese, magnesium, iron, zinc, aluminum, calcium, silicon, strontium, titanium, and combinations thereof. The powder additive may be applied via a variety of manners including employing a fluidized bed powder process as disclosed in U.S. Pat. Nos. 3,396,699; 4,084,018; 4,606,928; and 6,068,702.

The one or more nonwoven carrier webs that are ultimately laminated to the elastomeric layer are not initially substantially elastic in the cross-machine direction. The elastomeric layer can be processed through several transport stations, including an unwinding or de-festooning station, one or more slitting stations whereby the elastomeric layer and nonwoven carrier webs are cut to the desired dimension in the cross-machine direction, one or more laminating stations where the elastomeric layer is attached cofacially to one or more nonwoven carrier or additional nonwoven webs, one or more activation stations, where the laminate undergoes incremental stretching, and a winding station where the laminate is wound on a roll suitable for use in subsequent diaper converting operations.

The elastomeric layer may be bonded to the nonwoven carrier web by use of adhesives or other suitable means. Hot melt adhesives provide an especially useful means of laminating the elastomeric layer to the nonwoven carrier web. A variety of adhesive patterns are known in the art, such as spiral, meltblown, slot coated implementations including stripe patterns and continuous layers. Other means of laminating the elastomeric layer to the nonwoven can also be used, such as ultrasonic bonding and pressure bonding.

The basis weight of the nonwoven web of the elastic member should be from about 5 gsm, 9 gsm, or 14 gsm to about 27 gsm, 31 gsm, 42 gsm, or 50 gsm. Similarly, the elastic member may further comprise one or more additional nonwoven web layers that are adhesively bonded to the elastomeric layer. The one or more additional nonwoven webs may be laminated to the elastomeric layer and/or nonwoven carrier web before the lamination described above, before the elastomeric layer is wound onto a roll or festooned into packaging, forming an intermediate laminate. These one or more additional nonwoven webs have a basis weight of about 6, 7, or 8 gsm to about 10, 15, 20, 25, 20, or 35 gsm. For the production of the intermediate laminate and in order to achieve good functional properties of the resulting elastic member it is especially advantageous if the nonwoven carrier web of the elastic laminate and the additional nonwoven webs glued to the laminate are made of the same raw material. Possible raw materials these nonwoven carrier webs and/or additional nonwoven web layers include polyolefins. Additionally, these nonwoven web layers may include more than one layer of materials. For instance, the nonwoven carrier and additional nonwoven webs may be a material selected from the group consisting of spunbond nonwoven (S), spunbond/meltblown nonwoven (SM), spunbond/meltblown/spunbond (SMS) nonwoven, spunbond/meltblown/meltblown/spunbond (SMMS), spunbond/meltblown/meltblown/spunbond/spunbond (SMMSS), and combinations thereof. It is foreseeable that the additional nonwoven web layers that are adhered to the skinless elastomeric core layer and nonwoven carrier web may be made of differing raw materials on the same surface of the elastomeric layer as well as on opposing surfaces of the elastomeric layer (if more than one additional nonwoven web layer is employed). It is advisable that the additional nonwoven web layer(s) of the elastic laminate possess a dense fiber structure in order to ensure full coverage of the sticky elastomeric core layer whereas the nonwoven carrier web glued to the laminate can have a loose, possibly voluminous fiber structure.

The skinless elastomeric layer of the elastic laminate is preferably a layer of a single material or a mixture of materials wherein the materials selected from the group consisting of styrene isoprene styrene block copolymers, styrene butadiene styrene block copolymers, styrene ethylene butylene styrene block copolymers, polyurethane, ethylene copolymers, and combinations thereof. As with the elastomeric core layer, the elastic laminate can be unwound from its storage roll in a wide web and cut into strips. The strips are processed into equidistant positions and fed over transport rolls in parallel into a laminating unit, where the strips are laminated to one or more additional nonwoven webs. In an additional station the elastic areas of the nonwoven film laminate can be stretched in cross direction, preferably by ring-rolling in a stretching roll unit. Suitable stretching rolls are known from U.S. Pat. No. 4,834,741. Using the stretching rolls, the nonwoven film laminate is stretched in the cross direction. The stretching of the elastomeric core layer of the laminated strips is reversible; the stretching of the nonwoven carrier web and additional nonwoven web layer(s) is not, however. After passing the stretching unit, the elastic layer contracts and the stretched, inelastic irreversible layers also contract under the forces of the elastomeric layer and form folds which increase the volume of the elastic member. As mentioned earlier, a suitable stretching process is ring-rolling which reduces the elongation resistance of the nonwoven film laminate in the elastic areas.

In alternative embodiments, the elastic member of the present invention may comprise two or more elastomeric layer and nonwoven carrier web composites disposed in a face to face relationship. For instance, the layers would be configured with a nonwoven carrier web adhered to an elastomeric layer. A second elastomeric layer is then adhered to an opposing surface of the first elastomeric layer and a second nonwoven carrier web is adhered to a second surface of the second elastomeric layer. This embodiment would then be ring rolled as described herein as well.

Other Disposable Article Components

Figure 1:
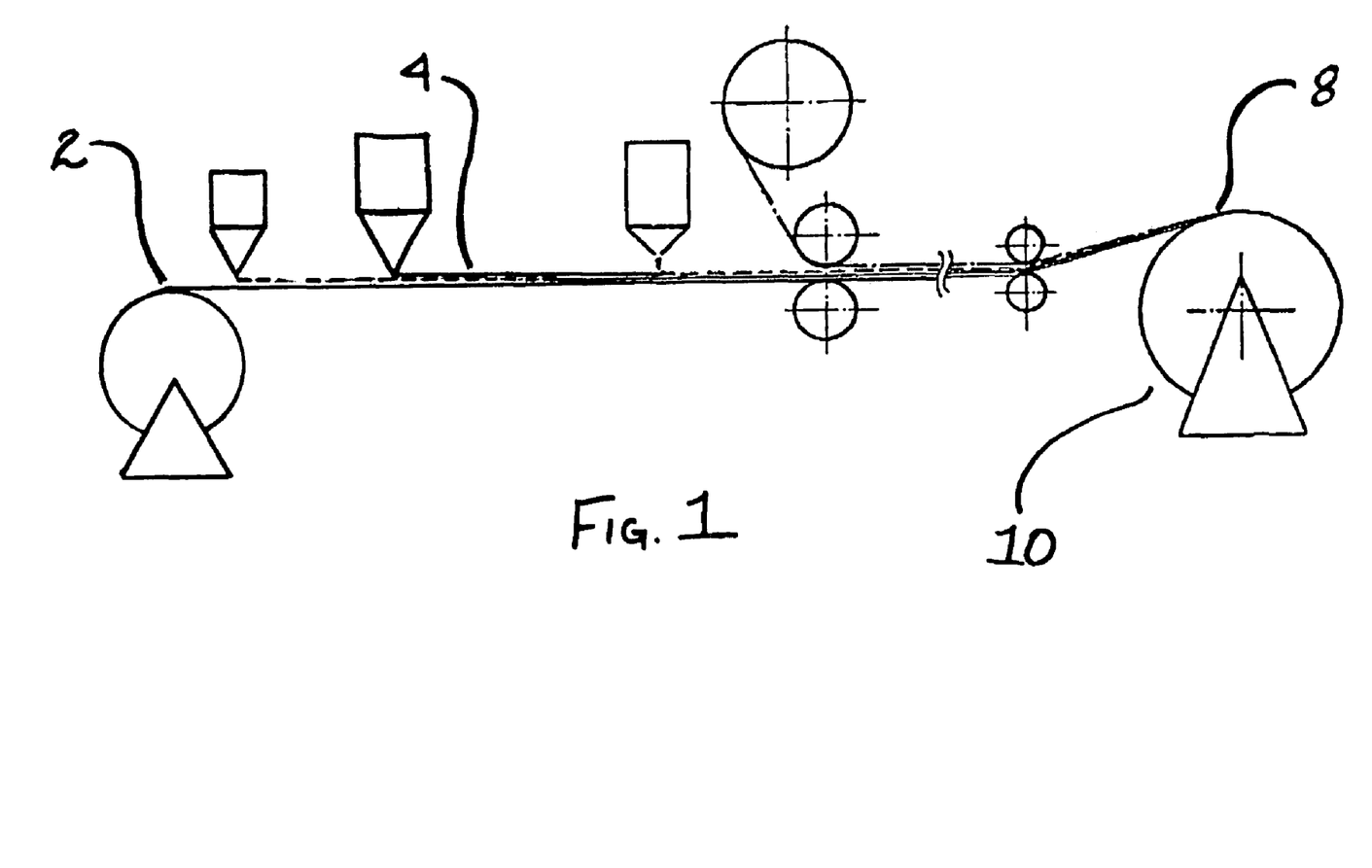
FIG. 1 shows a method for the production of an elastomeric member by adhesion lamination.

FIG. 1 depicts the invention's application process of a nonwoven carrier web 2 to a sticky elastomeric core layer 4 by adhesion lamination. The elastomeric layer 4 is extruded from a source of elastomeric material, e.g., an extruder. Before winding the elastomeric layer 4, a release liner 2 is disposed on a surface of the elastomeric layer 4 and an elastic member 8 is formed.

Figure 2:
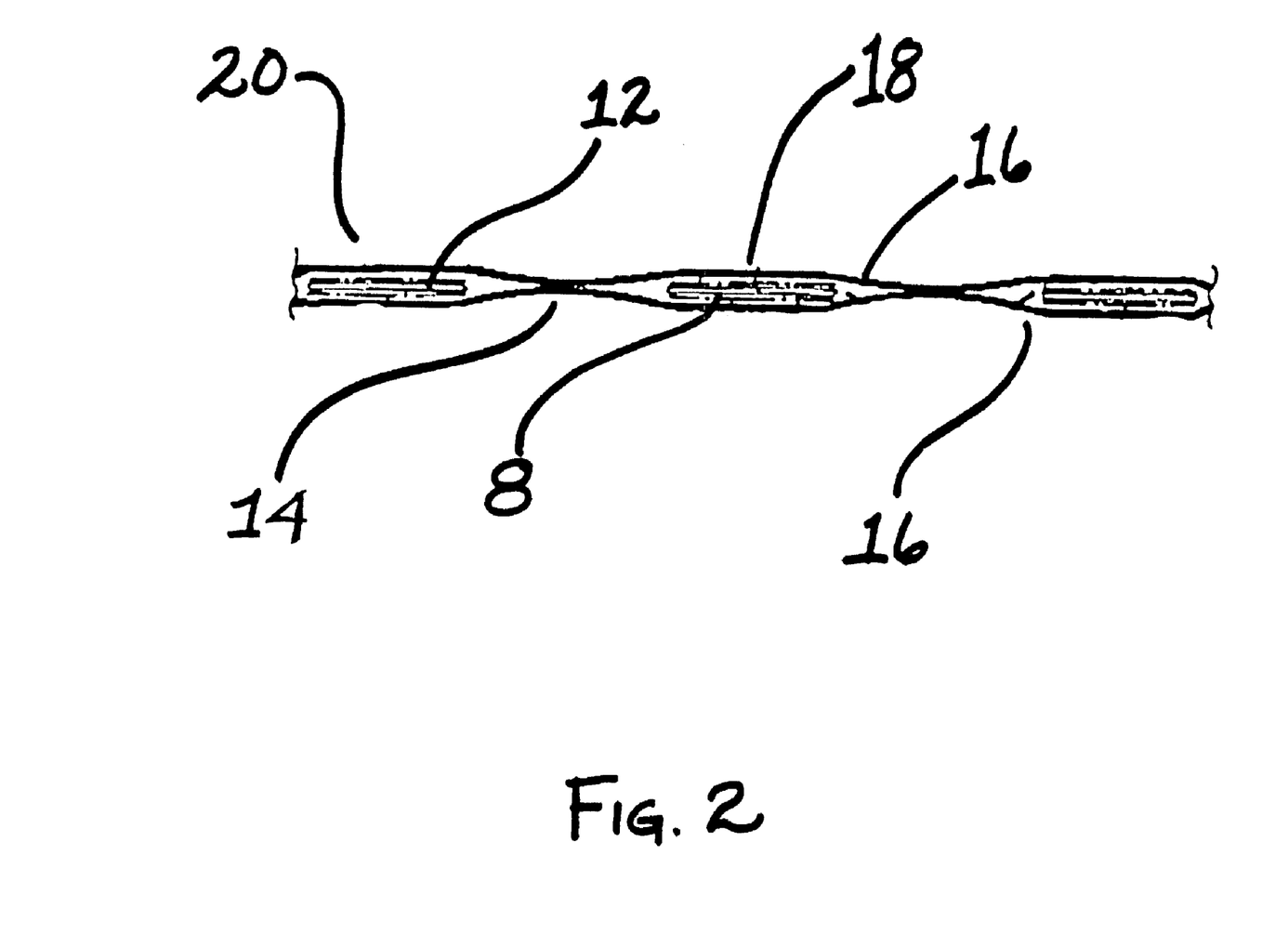
FIG. 2 shows a cross section of an elastic laminate containing a plurality of strips of the elastic member made with the method shown in FIG. 1.

The elastic member 8 produced according to FIG. 1 is then converted as roll stock material onto a storage roll 10 and used for the production of the disposable absorbent articles of the present invention. FIG. 2 illustrates a cross section of an elastic laminate 20 that includes strips of the elastic member 8 and two additional nonwoven webs 16 disposed on opposing surfaces of elastic member 8. This type of elastic laminate 20 is formed by unwinding the elastic member 8 from a storage roll 10 (as shown in FIG. 1), discarding of the release liner 2, applying a powder additive to prevent blocking, and cutting the member into strips 12. The strips 12 are placed into equidistant positions, in parallel into a laminating unit, where they are adhesively laminated onto or between one or more additional nonwoven webs 16. The additional nonwoven webs 16 are directly connected in the areas between the strips 12 and form the substantially inelastic areas 14. The areas of the elastic member 8 containing strips 12 form the substantially elastic areas 18. In an additional portion of the manufacturing process, the elastic member 8 is stretched in the cross direction in the substantially elastic areas 18 by a ring-rolling unit. The unit includes profiled rolls and these rolls elongate the elastic member 8 in the cross direction. The elongation of the elastomeric layer 2 is reversible, while the elongation of the additional nonwoven webs is not reversible. After passing the ring-rolling unit, the elastomeric layer 2 of the elastic member 8 contracts and the stretched and the additional nonwoven webs 16 form undulations or warpings, which increase the volume of the nonwoven layers.

Figure 3A:
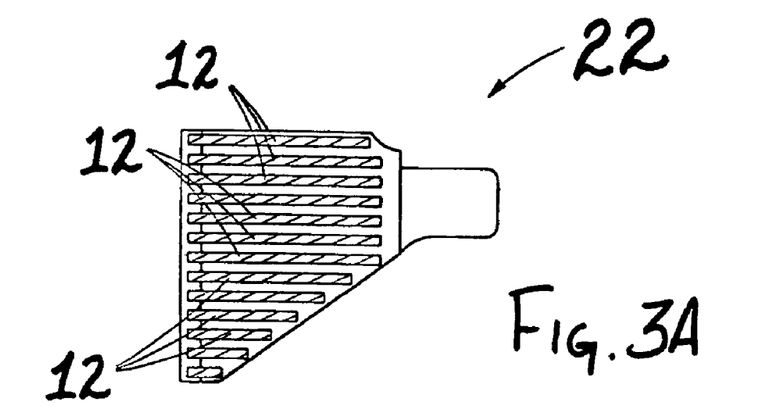
FIG. 3A-3C shows elastic side panels including the elastic members of the present invention.
Figure 3B:
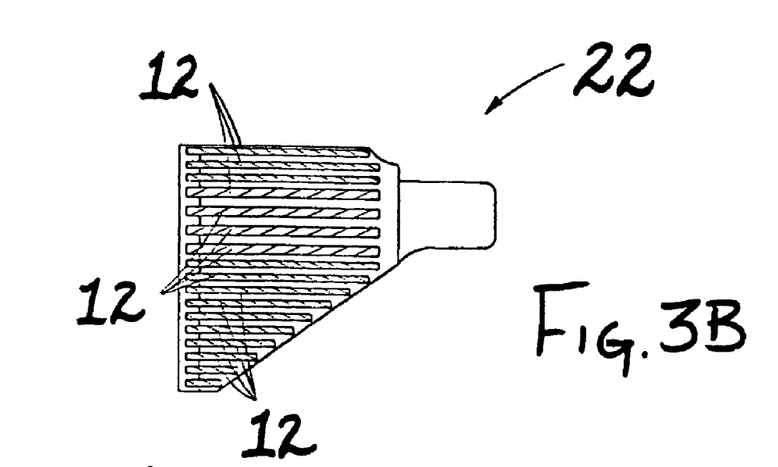
Figure 3C:
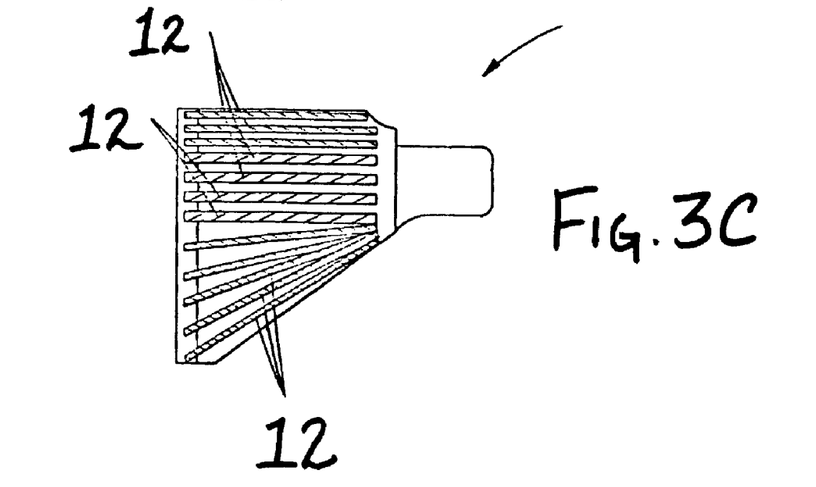

FIGS. 3A-3C each illustrate an elastic side panel 22 that includes strips 12 of elastic member 8. The strips 12 may be placed in the ear in a variety of configurations. In FIG. 3A, the strips 12 are placed parallel to one another and equidistanced from each other. In FIG. 3B, the strips 12 are cut into different widths to impart differential stretch across the ear's width. FIG. 3C includes different sized strips 12 that are placed in a combination of parallel and non-parallel positions to one another to impart various force vectors along the width of the diaper ear.

Figure 4:
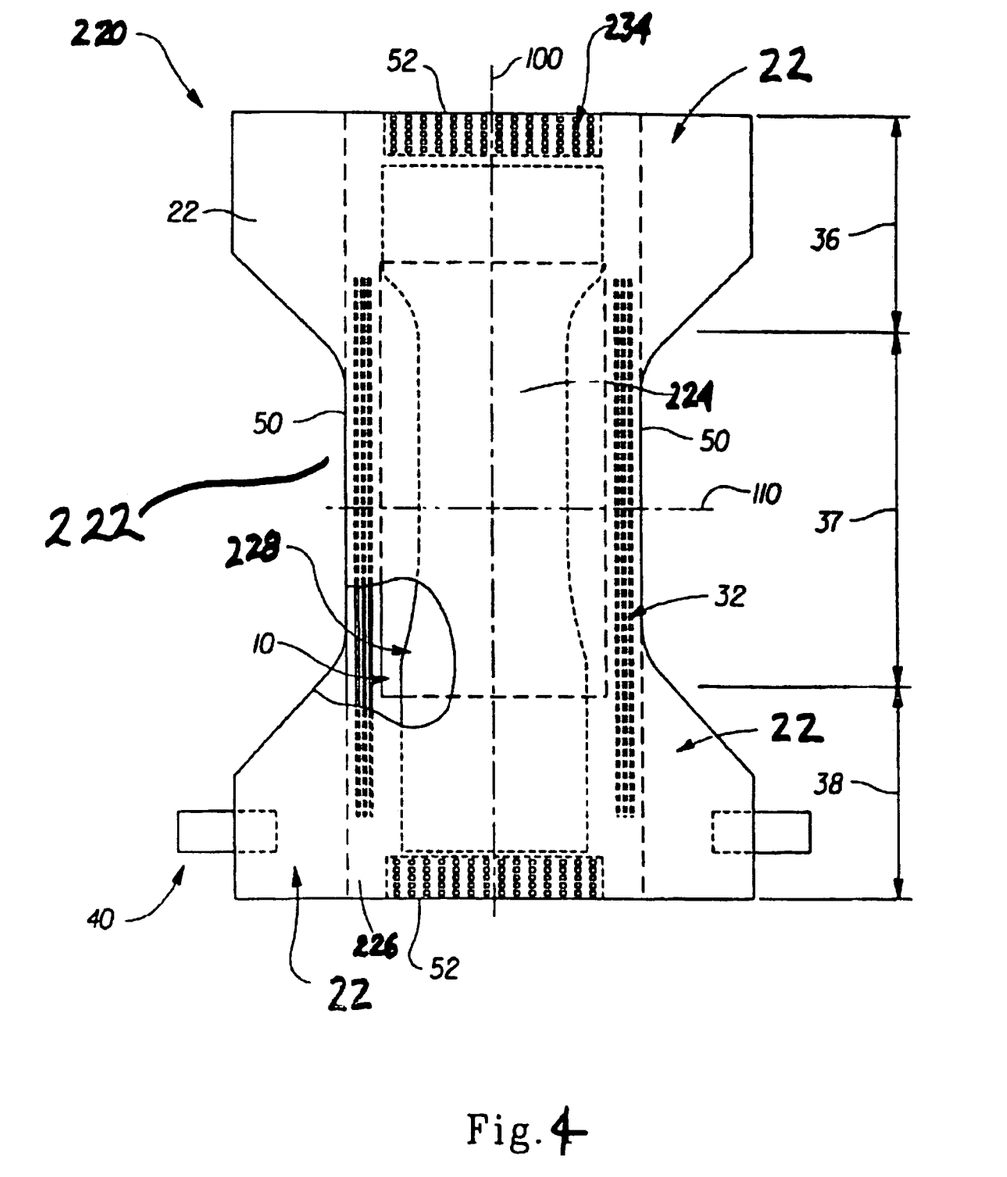
FIG. 4 shows a top plan view of a disposable absorbent article of the present invention, particularly with elastic side panels that include elastic members as claimed.

FIG. 4 is a plan view of the diaper 220 of the present invention in a flat-out, state with portions of the structure being cut-away to more clearly show the construction of the diaper 220. The portion of the diaper 220 which faces the wearer is oriented towards the viewer. As shown in FIG. 4, the diaper 220 preferably comprises a liquid pervious topsheet 224; a backsheet 226; an absorbent core 228 which is preferably positioned between at least a portion of the topsheet 224 and the backsheet 226; side panels 22; elasticized leg cuffs 32; an elastic waist feature 34; and a fastening system generally designated 40. The diaper 220 is shown in FIG. 4 to have a front waist region 36, a back waist region 38 opposed to the front waist region 36 and a crotch region 37 located between the front waist region 36 and the back waist region 38. The periphery of the diaper 220 is defined by the outer edges of the diaper 220 in which longitudinal edges 50 run generally parallel to the longitudinal centerline 100 of the diaper 220 and perpendicularly placed end edges 52 run between the longitudinal edges 50 generally parallel to the lateral centerline 110 of the diaper 220.

The chassis 222 of the diaper 220 comprises the main body of the diaper 220. The chassis 222 comprises at least a portion of the absorbent core 228 and preferably an outer covering including the topsheet 224 and/or the backsheet 226. If the absorbent article comprises a separate holder and a liner, the chassis 222 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 222 comprises the main structure of the diaper with other features added to form the composite diaper structure. While the topsheet 224, the backsheet 226, and the absorbent core 228 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999.

The backsheet 226 is generally that portion of the diaper 220 positioned adjacent a garment facing surface of the absorbent core 228 which prevents the exudates absorbed and contained therein from soiling articles which may contact the diaper 220, such as bed sheets and undergarments. In preferred embodiments, the backsheet 226 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper 220 while still preventing exudates from passing through the backsheet 226. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The backsheet 226, or any portion thereof, may be elastically extensible in one or more directions. In one embodiment, the backsheet 226 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996. In alternate embodiments, the backsheet 26 may comprise elastomeric films, foams, strands, or combinations of these or other suitable materials with nonwovens or synthetic films.

The backsheet 226 may be joined to the topsheet 224, the absorbent core 228 or any other element of the diaper 220 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 224 is preferably positioned adjacent a body surface of the absorbent core 228 and may be joined thereto and/or to the backsheet 226 by any attachment means known in the art. Suitable attachment means are described above with respect to means for joining the backsheet 226 to other elements of the diaper 220. In one preferred embodiment of the present invention, the topsheet 224 and the backsheet 226 are joined directly to each other in some locations and are indirectly joined together in other locations by directly joining them to one or more other elements of the diaper 220.

The topsheet 224 is preferably compliant, soft-feeling, and non-irritating to the wearer's skin. Further, at least a portion of the topsheet 224 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 224 includes fibers, the fibers may be spunbond, carded, wet-laid, meltblown, hydroentangled, or otherwise processed as is known in the art. One suitable topsheet 224 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 30 may be made in accordance with U.S. Pat. Nos. 4,609,518 and 4,629,643 issued to Curro et al. on Sep. 2, 1986 and Dec. 16, 1986, respectively. Such formed films are available from The Procter & Gamble Company of Cincinnati, Ohio as "DRI-WEAVE" and from Tredegar Corporation, based in Richmond, Va., as "CLIFF-T."

In certain embodiments, at least a portion of the topsheet 224 is made of a hydrophobic material or is treated to be hydrophobic in order to isolate the wearer's skin from liquids contained in the absorbent core 228. If the topsheet 224 is made of a hydrophobic material, preferably at least a portion of the upper surface of the topsheet 224 is treated to be hydrophilic so that liquids will transfer through the topsheet more rapidly. The topsheet 224 can be rendered hydrophilic by treating it with a surfactant or by incorporating a surfactant into the topsheet. Suitable methods for treating the topsheet 224 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 224 can be found in U.S. Statutory Invention Registration No. H1670 published on Jul. 1, 1997 in the names of Aziz et al. Alternatively, the topsheet 224 may include an apertured web or film which is hydrophobic. This may be accomplished by eliminating the hydrophilizing treatment step from the production process and/or applying a hydrophobic treatment to the topsheet 224, such as a polytetrafluroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 224 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; U.S. Pat. No. 5,968,025 entitled "Absorbent Article Having a Lotioned Topsheet" issued to Roe et al. on Oct. 19, 1999 and U.S. Pat. No. 6,716,441 entitled "Compositions for the efficient release of active ingredients" issued to Osborne on Apr. 6, 2004. The lotion may function alone or in combination with another agent as the hydrophobizing treatment described above. The topsheet 224 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished providing a more cloth like appearance.

The topsheet 224 may comprise one or more apertures to ease penetration of exudates there through, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the aperture should have an area of between about 10 $cm^2$ and about 50 $cm^2$. The aperture preferably has an area of between about 15 $cm^2$ and 35 $cm^2$.

Further, the topsheet 224 may be fully or partially elasticated or may be foreshortened so as to provide a void space between the topsheet 224 and the core 228. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets".

The absorbent core 228 may comprise any absorbent material which is generally compressible, conformable, non-irritating to the wearer's skin, and capable of absorbing and retaining liquids such as urine and other certain body exudates. The absorbent core 228 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 228 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 228 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994;

U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997.

The diaper 220 may also include a sublayer disposed between the topsheet 224 and the backsheet 226. (As used herein, the term "disposed" is used to mean that an element(s) of the diaper is formed (joined and positioned) in a particular place or position as a unitary structure with other elements of the diaper or as a separate element joined to another element of the diaper.) The sublayer may be any material or structure capable of accepting, storing or immobilizing bodily exudates. Thus, the sublayer may include a single material or a number of materials operatively associated with each other. Further, the sublayer may be integral with another element of the diaper 220 or may be one or more separate elements joined directly or indirectly with one or more elements of the diaper 220. Further, the sublayer may include a structure that is separate from the core 228 or may include or be part of at least a portion of the core 228.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 entitled "Disposable Absorbent Article Having Capacity to Store Low-Viscosity Fecal Material" issued to Roe on Jan. 20, 2004 and U.S. Pat. No. 5,941,864 entitled "Disposable Absorbent Article Having Improved Fecal Storage" issued to Roe on Aug. 24, 199. Further, the sublayer, or any portion thereof, may include or be coated with a lotion or other known substances to add, enhance or change the performance or other characteristics of the element.

The diaper 220 may also comprise at least one elastic waist feature 234 that helps to provide improved fit and containment. The elastic waist feature 234 is generally intended to elastically expand and contract to dynamically fit the wearer's waist. The elastic waist feature 234 preferably extends at least longitudinally outwardly from at least one waist edge of the absorbent core 228 and generally forms at least a portion of the end edge 52 of the diaper 220. Disposable diapers are often constructed so as to have two elastic waist features, one positioned in the first waist region 36 and one positioned in the second waist region 38. Further, while the elastic waist feature 234 or any of its constituent elements may comprise one or more separate elements affixed to the diaper 220, the elastic waist feature 234 may be constructed as an extension of other elements of the diaper 220, such as the backsheet 226, the topsheet 224, or both the backsheet 226 and the topsheet 224.

The elastic waist feature 234 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816, 025 issued to Foreman on Mar. 28, 1989.

The diaper 220 may also include a fastening system 40. The fastening system 40 preferably maintains the front waist region 36 and the back waist region 38 in a configuration so as to provide lateral tensions about the circumference of the diaper 220 to hold the diaper 220 on the wearer. The fastening system 40 preferably comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. No. 3,848, 594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. Pat. No. 6,432,098 entitled "Absorbent Article Fastening Device" in the names of Kline et al. issued on Aug. 13, 2002. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242, 436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997.

In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application Ser. No. 10/171,249, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The diaper 220 may also comprise side panels 22. One or more of the side panels 22 will most likely comprise the elastic member 8 and shall be elastic or extensible to provide a more comfortable and contouring fit by initially conformably fitting the diaper 220 to the wearer and sustaining this fit throughout the time of wear well past when the diaper 220 has been loaded with exudates since the elasticized side panels 22 allow the sides of the diaper 220 to expand and contract. The side panels 22 may also provide more effective application of the diaper 220 because even if the diaperer pulls one elasticized side panel 22 farther than the other during application, the diaper 220 will "self-adjust" during wear.

While the diaper 220 of the present invention preferably has the side panels 22 disposed in the back waist region 38, the diaper 220 may be provided with side panels 22 disposed in the front waist region 36 or in both the front waist region 36 and the back waist region 38.

The diaper 220 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Another component that may be included in the articles of the present invention is a hydrophobic surface coating as disclosed in U.S. Ser. No. 11/055,743 (P&G Case 9528M). This hydrophobic surface coating may be paired with the barrier coating of the present invention on the barrier layer or may be disposed adjacent to one or more additional components of the absorbent articles or composites of the present invention. For instance, this hydrophobic surface coating may be disposed on an interior surface of one or more leg cuffs, waist portions, or other areas of the absorbent article.

Embodiments of the present invention may also include pockets for receiving and containing waste, spacers which provide voids for waste, barriers for limiting the movement of waste in the article, compartments or voids which accept and contain waste materials deposited in the diaper 220, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; U.S. Pat. No. 6,168,584 entitled "Spacers For Use In Hygienic Absorbent Articles And Disposable Absorbent Articles Having Such Spacer" issued to Allen et al. on Jan. 2, 2001; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968, 312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,062,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Test Method

Energy Recovery Value

An MTS Alliance RT/1 tensile testing system may be used for the hysteresis testing necessary to determine the Energy Recovery Value. This Energy Recovery Value represents the percentage of energy that is expended and recovered in loading and unloading a sample of the elastomeric layer with a 100N load cell to an extension of 200%. In particular, the hysteresis system used for this determination is configured to acquire force data while imposing a regimen of displacement (i.e., tensile) on an elastic member specimen. The system is fitted with a 100N load cell (supplied by MTS) and a set of custom fabricated grips of the design shown in FIG. 5 (line contact with opposing rubber face, with screw action clamp.) Suitable alternative grips include MTS part numbers 056-163-829 (line contact grip faces) and 100-036-576 (pneumatically actuated grips). The grips should hold the specimen during the hysteresis test with no appreciable slippage or damage, thereby providing well-defined lines of contact on the specimen. The engineering strain e is defined as $$e = (L-L_0)/L_0 = z/L_0$$

where:
- Gauge length, $L_0$, is the distance between lines of grip contact when the undeformed elastic member specimen is mounted in the grips. The $L_0$ in the present examples is 25.4 mm.
- Grip position, L, is the distance between lines of grip contact during the hysteresis test.
- Displacement, z, is defined as $z=L-L_0$.

The parameters listed directly below should be used for the hysteresis testing.

Number of stretch/unstretch cycles: 1
ambient temperature: 21-24 C
stretching direction: TD
Gauge Length: 25.4 mm
Specimen Width: 19 mm
Crosshead speed: 4.23 mm/s (10 inches/min.)

In order to prepare for the hysteresis testing, a sharp Xacto knife and a metal straight edge are used to cut an elastic member specimen 19 mm wide by approximately 30 mm long. In the instance of this particular testing, the 30 mm dimension coincided with the laminate's transverse direction (also known as the cross-machine direction.) The grip position L is set to 25.4 mm. The specimen was mounted in the grips with good alignment and with no appreciable slack or stretching. The table below shows these steps and the displacement regimen carried out by the system. The forces are recorded in newtons and then are subsequently converted to N/cm (1.9 cm specimen width.)

| Displacement Regimen for Laminate Hysteresis | | | | | | | |
|---|---|---|---|---|---|---|---|
| Step | Z start (mm) | Z end (mm) | L start (mm) | L end (mm) | e start (unit­less) | e end (unit­less) | Speed (mm/s) | Hold time (s) |
| Mount specimen | 0 | 0 | 25.4 | 25.4 | 0 | 0 | N/A | N/A |
| Pre-jog | 0 | −5 | 25.4 | 20.4 | 0 | slack | * | N/A |
| Load | −5 | 25.4 | 20.4 | 50.8 | Slack | 1 | 4.23 | N/A |
| Hold | 25.4 | 25.4 | 50.8 | 50.8 | 1 | 1 | 0 | 30 |
| unload | 25.4 | −5 | 50.8 | 20.4 | 1 | slack | 4.23 | N/A |

*not critical

The pre-jog step is purely a matter of personal preference. It is not mandatory, but allows the crosshead to come up to speed before tensile deformation of the specimen begins.

Film PreStretch and Hysteresis

A sharp Xacto knife and a metal straightedge are again used to cut a specimen of the elastic member that is 19 mm wide by approximately 30 mm long. The specimen's long dimension coincides with the film's transverse direction (also known as the cross-machine direction.) The specimen's long dimension is measured with a scale to the nearest 0.2 mm and weighed on a 4 place lab balance. The grip position L is set to 25.4 mm. The specimen is mounted in the grips with good alignment and with no appreciable slack or stretching. The table below shows these steps and the displacement regimen carried out by the system.

| Displacement Regimen for Film Pre-stretch | | | | | | | |
|---|---|---|---|---|---|---|---|
| Step | Z start (mm) | Z end (mm) | L start (mm) | L end (mm) | e start (unit­less) | e end (unit­less) | Speed (mm/s) | Hold time (s) |
| Mount specimen | 0 | 0 | 25.4 | 25.4 | 0 | 0 | N/A | N/A |
| Pre-jog | 0 | −5 | 25.4 | 20.4 | 0 | slack | * | N/A |
| Load | −5 | 127 | 20.4 | 152.4 | Slack | 5 | 4.23 | N/A |
| Hold | 127 | 127 | 152.4 | 152.4 | 5 | 5 | 0 | 1 |
| Unload | 127 | −5 | 152.4 | 20.4 | 5 | slack | 4.23 | N/A |

*Not critical

After the PreStretch cycle is complete, the specimen is removed from the grips, re-gripped, (grip position L was 25.4 mm) again with good alignment and no appreciable slack or stretching. If needed, the specimen's length is cut to about 30 mm length to accommodate the grip bolt during re-gripping. The table below shows these steps and the displacement regimen carried out by the system. The hysteresis test commences about 120 seconds after the PreStretch is complete.

| Displacement Regimen for Film Hysteresis | | | | | | | |
|---|---|---|---|---|---|---|---|
| Step | Z start (mm) | Z end (mm) | L start (mm) | L end (mm) | e start (unit­less) | e end (unit­less) | Speed (mm/s) | Hold time (s) |
| Mount specimen | 0 | 0 | 25.4 | 25.4 | 0 | 0 | N/A | N/A |
| Pre-jog | 0 | −5 | 25.4 | 20.4 | 0 | slack | * | N/A |
| Load | −5 | 50.8 | 20.4 | 76.2 | Slack | 2 | 4.23 | N/A |
| Hold | 50.8 | 50.8 | 76.2 | 76.2 | 2 | 2 | 0 | 30 |
| Unload | 50.8 | −5 | 76.2 | 20.4 | 2 | slack | 4.23 | N/A |

The forces is recorded in newtons, then subsequently converted to engineering stress by the formula $$\text{Engineering stress (MPa)} = 1e-6 * F * D_v / D_l$$

where

F is the force in Newtons $D_v$ is the specimen's volume density (assumed 950 kg/m3.)

$D_l$ is the specimen's mass per unit length, derived from the mass and length measurements described in the Film Pre-Stretch description above.

The Energy Recovery Value (ERV) is then determined by the formula $$ERV = \frac{\text{Area under UnLoad curve}}{\text{Area under Load curve}} = \frac{\int_{UnLoading} F dz}{\int_{Loading} F dz}$$

Where F and z are the force and displacement respectively, and the integral in the numerator is evaluated during the "UnLoad" step and the integral in the denominator is evaluated for the "Load" step.

EXAMPLES

Example 1

A disposable article according to the present invention is made as follows. An elastomeric layer including 75 wt % Vector 4211 (Dexco Polymers), 15 wt % PS 3900 (Novachem), and 10 wt % white mineral oil (Drakeol Supreme from Pennreco) is extruded on a Berstorff Z25x32D twin screw extruder equipped with an Arbo vibratory loss-in-weight feeder. The extruder's temperature zones are set in an upward ramping profile ranging from 300° F. near the feed throat to 400° F. where the elastomer exits the extruder. The temperature of all subsequent zones of the melt path (adapter block and a Davis Standard 6 inch sheeting die oriented vertically) are set at 400° F. Fifteen hundred ppm of Irganox 1010 is added to the elastomer to improve thermal stability and the elastomeric layer is extruded directly onto double-sided release paper (fed onto a chill roll) and wound onto a storage roll. The skinless elastomeric layer is subsequently removed from the release paper and subjected to an electrostatic fluidized bed powder treatment (Electrostatic Technology, Inc., 4 Pin Oak Drive, Branford, Conn. 06405). A voltage of 50 kV was used for all specimens. Exposure time and distance between film and bed were varied to achieve various add-on rates of powder to film. Exposure times were varied from 500-4000 ms. Distance between powder bed and film were varied from 5-10 cm. Powders used include the following: Vertal 92 produced by Luzenac Inc., Nan-O-Sil Lot #284-T30-15 produced by Energy Strategy Associates, Inc., Mica powder (60 mesh), and polyethylene powder.

The skinless elastomeric layer is then adhesively laminated between two additional nonwoven webs and the resultant elastic laminate is incrementally stretched as disclosed in U.S. Pat. No. 4,834,741. The adhesive can be applied to the nonwoven, then brought in contact with the film and subsequently run through a nip roll. The adhesive can be applied in a striped pattern such that the direction of the stripes runs perpendicular to the direction of laminate extensibility in the final product. The elastic laminate is then cut into a suitable size to form an elastic side panel and is bonded to a chassis of a diaper or pull-on training pant by hot melt adhesive, pressure bonding, or a combination of each. A hot melt adhesive is applied to the back ear, chassis, or both. Then the back ear is applied to the chassis. To further strengthen the connection of the back ear and the chassis, mechanical bonds are also used. A variety of mechanical bonds are known in the art. One such mechanical bond is a pressure bond, which involves applying high pressure at a bond site to compress the materials to be joined. Particularly with polymeric materials, the pressure causes the materials to flow together and mutually fuse. A plurality of bond sites are created, arranged along the entire bond between chassis and back ear.

Comparative Example 1

The article of Example 1 is constructed as described above with the elastomeric layer of Example 1 being replaced with Tredegar's X-31794 elastomeric film which is commercially available from Tredegar Film Products of Richmond, Va.

Example 2

The article of Example 1 is constructed as described above with the elastomeric layer of Example 1 being replaced with Nordenia's TK20913 elastomeric film which is commercially available from Nordenia Deutschland Gronau of Germany.

Comparative Example 2A

The article of Example 1 is constructed as described above with the elastomeric layer of Example 1 being replaced with Nordenia's KG6361.000 elastomeric film which is commercially available from Nordenia Deutschland Gronau of Germany.

Comparative Example 2B

The article of Example 1 is constructed as described above with the elastomeric layer of Example 1 being replaced with Nordenia's KG6356.xxx elastomeric film which is commercially available from Nordenia Deutschland Gronau of Germany.

| Example | Energy Recovery Value | Load 2 (MPa) | UnLoad 0.30 (MPa) | UnLoad 0.50 (MPa) |
| --- | --- | --- | --- | --- |
| Example 1 | 0.86 | 0.92 | 0.28 | 0.39 |
| Comparative 1 | 0.63 | 1.04 | 0.14 | 0.24 |
| Example 2 | 0.79 | 1.24 | 0.37 | 0.55 |
| Comparative 2a | 0.63 | 1.22 | 0.23 | 0.38 |
| Comparative 2b | 0.74 | 1.21 | 0.32 | 0.48 |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A disposable absorbent article which comprises a chassis having a front waist region, a back waist region, and a crotch region between the front and back waist regions, said chassis having two opposing longitudinal edges and two perpendicularly placed end edges, said chassis further comprising:
   a. a liquid permeable topsheet spanning at least the crotch region;
   b. a backsheet spanning at least the crotch region;
   c. an absorbent core disposed between said topsheet and backsheet; and
   d. an elastic member disposed along at least one opposing longitudinal edge in either the front waist or back waist region of said chassis wherein said member comprises a non-breathable, unapertured, skinless elastomeric layer selected from the group consisting of styrene isoprene styrene block copolymers, styrene butadiene styrene block copolymers, styrene ethylene butylene styrene block copolymers, and combinations thereof, wherein said elastic member takes the form of three or more strips placed in parallel, non-parallel or a combination of parallel and non-parallel positions to one another on or between one or more additional nonwoven webs, wherein the elastomeric layer is subjected to an anti-blocking treatment comprising treatment with a powder additive prior to lamination with said one or more additional nonwoven webs that prevents the elastomeric layer from sticking to itself prior to such lamination with said one or more additional nonwoven webs, wherein said treatment of the elastomeric layer with a powder additive comprises application of the powder to one or both surfaces of the elastomeric layer, and wherein said elastomeric layer exhibits an Energy Recovery Value of at least about 0.77.

2. The article according to claim 1 wherein said elastic member is included in a disposable article component that is selected from a group consisting of elastic side panels, leg cuffs, waistbands, outer covers, landing zones, and combinations thereof.

3. The article according to claim 1 wherein said elastic member is included in an elastic side panel that is disposed along at least one longitudinal edge of said chassis.

4. The article according to claim 1 wherein said layer exhibits an Energy Recovery Value of at least about 0.79.

5. The article according to claim 1 wherein said layer exhibits an Energy Recovery value of at least about 0.83.

6. The article according to claim 1 wherein the powder is selected from the group consisting of talc, mica, mullite, calcium carbonate, silica, powdered polyethylene, corn starch, barium sulfate, gypsum, activated carbon, polyolefin, alginate, aluminum silicate, bentonite, carbon black, carbon nanotubes, chalk, cobalt acetate, dicalite perlite, dolomite calfix, flour, graphite, hydroxy ethyl cellulose, kaolin, polyethylene wax, polyvinyl alcohol, rice flour, starch, modified starch, super absorbent, vermiculite, wax powder, oxides of bismuth, cerium, zirconium, manganese, magnesium, iron, zinc, aluminum, calcium, silicon, strontium and titanium, and combinations thereof.

7. The article according to claim 6 wherein the powder is selected from the group consisting of calcium carbonate, talc, corn starch, and combinations thereof.

8. The article according to claim 3 wherein the elastic side panel is disposed along at least one longitudinal edge of said chassis in said back waist region.

9. The article according to claim 3 wherein the elastic side panel is disposed along at least one longitudinal edge of said chassis in said front waist region.

10. A disposable absorbent article which comprises a chassis having a front waist region, a back waist region, and a crotch region between the front and back waist regions, said chassis having two opposing longitudinal edges and two perpendicularly placed end edges, said chassis further comprising:

a. a liquid permeable topsheet spanning at least the crotch region;
b. a backsheet spanning at least the crotch region;
c. an absorbent core disposed between said topsheet and backsheet;
d. an elastic member that is an elastic side panel disposed along at least one opposing longitudinal edge in either the front waist or back waist region of said chassis wherein said member comprises a non-breathable, unapertured, skinless elastomeric layer selected from the group consisting of styrene isoprene styrene block copolymers, styrene butadiene styrene block copolymers, styrene ethylene butylene styrene block copolymers, and combinations thereof, wherein said elastic member takes the form of three or more strips placed in parallel, non-parallel or a combination of parallel and non-parallel positions to one another on or between one or more additional nonwoven webs, wherein the elastomeric layer is subjected to an anti-blocking treatment comprising treatment with a powder additive prior to lamination with said one or more additional nonwoven webs that prevents the elastomeric layer from sticking to itself prior to such lamination with said one or more additional nonwoven webs, wherein said treatment of the elastomeric layer with a powder additive comprises application of the powder to one or both surfaces of the elastomeric layer, and wherein said elastomeric layer exhibits an Energy Recovery Value of at least about 0.77; and e. a fastener attached to an outermost edge of said side panel.

11. The article of claim 10 wherein said fastener is selected from the group consisting of tape tabs, hook and loop fastening components, interlocking fasteners, and combinations thereof, wherein the interlocking fasteners are selected from the group consisting of tabs & slots, buckles, buttons, snaps, and/or hermaphroditic fastening components.

12. The article according to claim 7 wherein the powder is corn starch.

13. The article according to claim 10 wherein the powder is selected from the group consisting of talc, mica, mullite, calcium carbonate, silica, powdered polyethylene, corn starch, barium sulfate, gypsum, activated carbon, polyolefin, alginate, aluminum silicate, bentonite, carbon black, carbon nanotubes, chalk, cobalt acetate, dicalite perlite, dolomite calfix, flour, graphite, hydroxy ethyl cellulose, kaolin, polyethylene wax, polyvinyl alcohol, rice flour, starch, modified starch, super absorbent, vermiculite, wax powder, oxides of bismuth, cerium, zirconium, manganese, magnesium, iron, zinc, aluminum, calcium, silicon, strontium and titanium, and combinations thereof.

14. The article according to claim 13 wherein the powder is selected from the group consisting of calcium carbonate, talc, corn starch, and combinations thereof.

15. The article according to claim 14 wherein the powder is corn starch.

* * * * *